(12) United States Patent
Noda

(10) Patent No.: US 6,602,243 B2
(45) Date of Patent: Aug. 5, 2003

(54) FOLEY CATHETER HAVING REDUNDANT TEMPERATURE SENSORS AND METHOD

(75) Inventor: Wayne Noda, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/816,288

(22) Filed: Mar. 21, 2001

(65) Prior Publication Data

US 2002/0082587 A1 Jun. 27, 2002

Related U.S. Application Data

(60) Provisional application No. 60/256,083, filed on Dec. 15, 2000.

(51) Int. Cl.[7] .................... A61M 27/00; A61B 5/00; A61E 7/00; A61E 7/12
(52) U.S. Cl. .............. 604/544; 600/549; 607/106; 607/105; 607/104; 607/113
(58) Field of Search ............... 604/544, 533–536, 604/538, 539, 284; 600/549; 607/96, 105, 106, 113, 104

(56) References Cited

U.S. PATENT DOCUMENTS

| | | | | |
|---|---|---|---|---|
| 4,322,594 A | * | 3/1982 | Brisson | ............... 600/549 |
| 4,497,324 A | * | 2/1985 | Sullivan et al. | ............ 600/549 |
| 5,249,585 A | * | 10/1993 | Turner et al. | |
| 6,009,351 A | * | 12/1999 | Flachman | |
| 6,019,783 A | * | 2/2000 | Philips et al. | |
| 6,126,684 A | * | 10/2000 | Gobin et al. | |
| 6,146,411 A | * | 11/2000 | Noda et al. | |
| 6,290,717 B1 | * | 9/2001 | Philips | |
| 6,419,643 B1 | * | 7/2002 | Shimada et al. | |
| 2002/0077680 A1 | * | 6/2002 | Noda | ......................... 600/549 |

* cited by examiner

Primary Examiner—Karin Reichle
(74) Attorney, Agent, or Firm—Burns, Doane, Swecker & Mathis, L.L.P.

(57) ABSTRACT

A Foley catheter has redundant temperature sensors to enable use of the Foley catheter with a patient heating system, such as one relying on a vascular heat exchange catheter. The temperature sensors electronically couple with a control unit, which obtains a primary temperature reading from one of the temperature sensors and obtains a secondary temperature reading from the other temperature. The control unit compares the primary and secondary temperature reading to determine a sensor temperature difference. When the sensor temperature difference exceeds a predetermined value, then the control unit activates an alarm, shuts down the patient heating system, or both.

7 Claims, 5 Drawing Sheets

FOLEY CATHETER HAVING REDUNDANT TEMPERATURE SENSORS AND METHOD

CROSS-REFERENCE TO RELATED APPLICATION:

This patent application claims the benefit of U.S. Provisional Application Serial No. 60/256,083, filed on Dec. 15, 2000.

FIELD

This invention relates to Foley Catheters, and particularly Foley Catheters having temperature sensors.

INCORPORATION BY REFERENCE

The disclosures of U.S. Pat. No. 6,019,783, issued Feb. 1, 2000, U.S. Pat. No. 6,126,684, issued Oct. 3, 2000, and U.S. Pat. No. 6,146,411, issued Nov. 14, 2000, are incorporated herein by reference.

BACKGROUND

Foley catheters typically include a soft, thin rubber tube with a balloon on one end. The catheter is threaded through the urinary duct (urethra) and into the bladder to drain urine from the bladder. A Foley catheter is typically used when normal urination is disrupted by an infection, a swollen prostate gland, bladder stones, or, sometimes, an injury. In very sick people, a catheter may be used to keep track of urine production.

A typical Foley catheter has drainage lumen, and an inflation lumen for inflating and deflating the balloon. The balloon is normally deflated until properly positioned in a patient's bladder. Once the catheter is properly positioned, the inflation lumen delivers fluid to inflate the balloon. The inflated balloon holds the catheter in place.

There are risks associated with the use of a Foley catheter. For example, the bladder or urethra could be injured when the Foley catheter is inserted. Infection is also possible. Patients may find the process of insertion of a Foley catheter unpleasant and sometimes painful.

The bladder is an accepted situs for core body temperature measurements. Accordingly, some Foley catheters include a temperature sensor included on the end of the catheter. A wire connects the sensor, via the catheter, to externally located monitoring devices.

One drawback to Foley catheters with a temperature sensor is that the sensor may fail. When the sensor fails, the failed catheter may have to be replaced. This not only compounds patient discomfort, but also increases the risk of injury and infection for the patient. A further risk is that the failure will not be detected and that other systems might depend on the erroneous temperature sensor reading. For example, a patient heating or cooling system may fail to properly operate when relying on temperature measurement provided by a failed temperature sensor.

What is desired is a way to measure a patient's core body temperature while minimizing patient discomfort and risk of injury. What is also desired is a way of assuring integrity of core body temperature measurements.

SUMMARY

A Foley catheter having redundant temperature sensors includes a catheter body with a proximal end and a distal end, an inflatable balloon disposed near the distal end, an inflation lumen extending from the proximal end to the balloon for inflating and deflating the balloon, a drainage lumen extending from the proximal end to the distal end, at least one temperature sensor lumen extending from the proximal end to the distal end, and at least two temperature sensors, each having a wire and a sensor element, the sensor elements being disposed in the distal end of the catheter body and the wires extending through the catheter body drainage lumen.

The temperature sensors electronically couple with a control unit, which obtains a primary temperature reading from one of the temperature sensors and obtains a secondary temperature reading from the other temperature sensors. The control unit compares the primary and secondary temperature reading to determine a difference.

The control unit establishes a threshold. The threshold is the maximum acceptable difference between the primary and secondary temperature readings. This threshold, according to one aspect of the invention, is set manually by an operator. The control unit also includes an alarm so that when the difference between the primary and secondary temperature readings exceeds the threshold, the control unit activates the alarm.

The alarm is audible according to one aspect of the invention and is sounded on a speaker in communication with the control unit. According to another aspect of the invention, the alarm includes a video display and activation of the alarm provides a video signal to the video display. In yet another embodiment, the alarm simply shuts the control unit off.

A method of using a Foley catheter with redundant temperature sensors in accordance with the invention includes the steps of introducing a Foley catheter into the bladder of a patient and using the Foley catheter to drain urine from the bladder. The method also includes electronically coupling the temperature sensors to a control unit and activating the control unit to obtain the primary temperature reading and the secondary temperature reading from the redundant temperature sensors.

Obtaining two, or more, temperature readings facilitates redundancy. One aspect of the invention includes the step of comparing the primary temperature reading and the secondary temperature reading to determine whether both sensors are operational.

Another aspect of the invention includes three temperature sensors and an appropriate methodology for detecting sensor failure. Three sensors enables continued operation of the control unit to achieve meaningful temperature readings notwithstanding the failure of one of the temperature sensors. It can be appreciated that there are a variety of control and feedback methods that can accomplish continuous operation of the catheter, sensors and control unit during a failure of one of the sensors.

According to an aspect of the invention having two sensors, determining whether both sensors are operational is accomplished by comparing the primary temperature reading and the secondary temperature reading to determine a difference between the primary and secondary temperature readings. The control unit deactivates when the difference exceeds the threshold. Preferably, the sensors operate with an accuracy of +/−0.1 degree Fahrenheit. Accordingly a temperature difference of a whole degree, for example, or more would typically indicate failure of one of the sensors.

According to an embodiment of the invention the controller establishes a temperature threshold within the range of 0.5–2 degrees Fahrenheit. More preferably, however, the temperature threshold is about 1 degree Fahrenheit so that the redundant sensors would operate safely in conjunction with a heat exchange catheter system for regulating patient body temperature.

DETAILED DESCRIPTION

Figure 1:
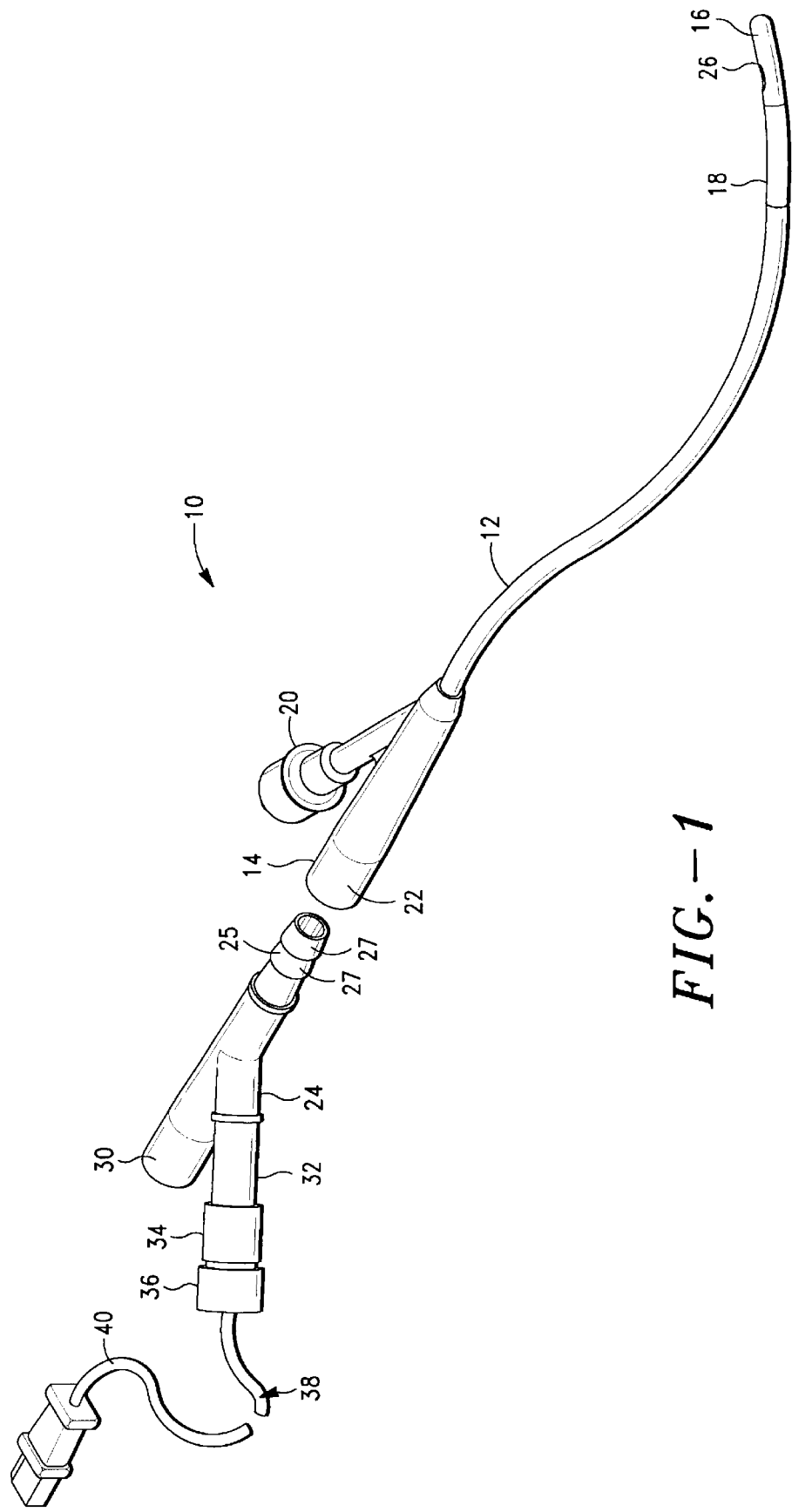
FIG. 1 is a perspective view of a Foley catheter and the adapter in accordance with the present invention.

FIG. 1 shows a Foley catheter generally designated with the reference numeral 10. The catheter 10 includes a catheter body 12 with a proximal end 14 and a distal end 16. The catheter 10 also includes a balloon 18, an inflation lumen 20, a drainage lumen 22, and an adapter 24.

The balloon 18 is deflated for insertion into a patient. The balloon 18 is disposed near the distal end 16. The inflation lumen 20 extends within the catheter body 12 from the proximal end 14 to the balloon 18, in fluid communication with the balloon 18, for inflating and deflating the balloon 18.

The catheter drainage lumen 22 extends from the proximal end 14 to the distal end 16. The distal end 16 includes an opening 26 in fluid communication with the drainage lumen 22 to facilitate drainage of urine from the bladder of a patient.

The adapter 24 has a drainage lumen 30, a temperature sensor lumen 32 and a connector 25. The connector 25 attaches to the proximal end 14 of the catheter body 12. The connector 25 establishes fluid communication between the adapter drainage lumen 30 and the catheter drainage lumen 22. Preferably the connector 25 is tapered and includes ribs 27 for insertion and press-fit into the proximal end 14 of the catheter body 12.

Figure 2:
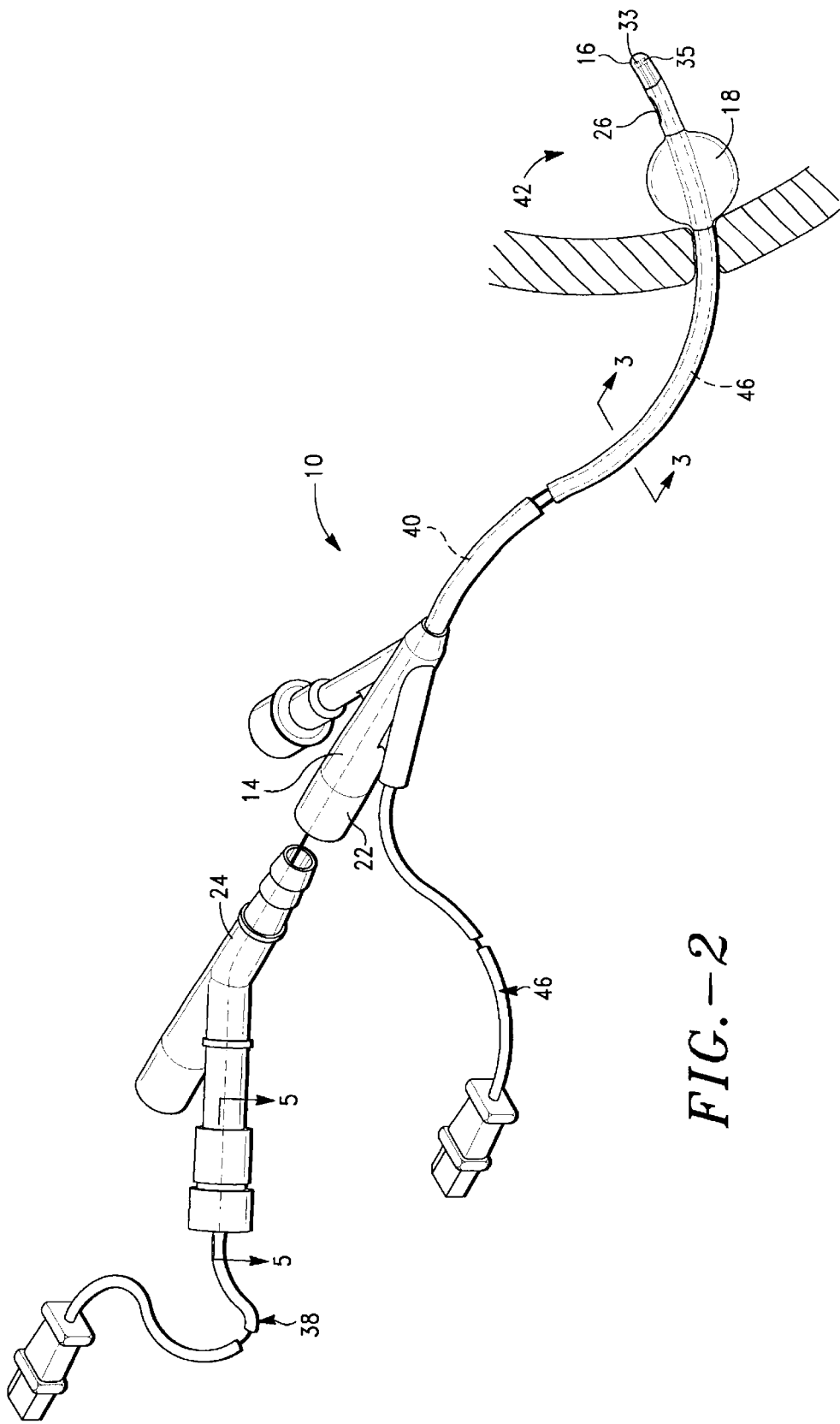
FIG. 2 is a perspective view of a Foley catheter inserted into a patient and the adapter in accordance with the present invention.

The adapter temperature sensor lumen 32 includes a fitting 34 and a cap 36. The temperature sensor 38 has a wire 40 and a distally located sensor element 33 (FIG. 2). The fitting 34 is fixed on the temperature sensor lumen 32 of the adapter 24. Preferably the fitting 34 bonds to the temperature sensor lumen 32. The fitting 34 receives the cap 36. The cap 36 and a portion of the fitting 34 are threaded to enable the cap 36 to rotate onto the fitting 34. The cap 36 is rotatable to adjustably torque the cap 36 onto the fitting 34.

The temperature sensor wire 40 normally slides through the cap 36, the fitting 34, the connector 25, and the catheter drainage lumen 22. The temperature sensor 38 includes a distally mounted temperature sensor element 33 (FIG. 2) that seats in the distal end 16 of the catheter body 12. Rotating the cap 36 with respect to the fitting 34 selectively anchors the wire 40 with respect to the adapter 24 to prevent movement of the sensor element 33.

FIG. 2 shows the Foley catheter 10 inserted into the bladder 42 of a patient. The Foley catheter 10 includes an integrated temperature sensor 46 with an integrated sensor element 35 disposed at the distal end 16 of the catheter body 12.

During normal operation of the Foley catheter 10, the catheter 10 is introduced into the bladder 42 of a patient. The balloon 18 inflates to hold the catheter 10 in the bladder 42. Urine drains from the bladder 42 through the opening 26 and via the catheter drainage lumen 22. The integrated sensor 46 with the sensor element 35 senses the patient's bladder temperature.

The adapter 24 attaches to the proximal end 14 of the catheter body 12. An operator manually advances the temperature sensor wire 40 to slide the temperature sensor wire 40 and sensor element 33 via the drainage lumen, towards the distal end 16 of the catheter body 12. Preferably, the temperature sensor wire 40 slides the temperature sensor element 33 fully to the distal end 16 of the catheter body 12.

According to one method of using the invention, the integrated temperature sensor 46 fails. This failure is detected. The Foley catheter 10 remains in the bladder 42. The adapter 24 of the present invention then attaches to the proximal end 14 of the catheter and the sensor 38 with the sensor element 33 advances through the drainage lumen of the Foley catheter 10 to position the sensor element 33 in the distal end 16 of the catheter body 12.

The sensor element 35 and the sensor element 33 are collocated for redundancy and improved accuracy. The sensor elements 33 and 35 provide a primary and secondary measure, respectively, of core body temperature. The secondary measure of temperature is used in conjunction with primary temperature measurements for improved temperature sensing accuracy and reliability.

Collocated temperature sensor elements 33 and 35 are also useful for communicating with discrete monitoring and data compilation devices requiring temperature input, such as a discrete patient data recorder and a medical device, for examples.

It can be appreciated that sensor element collocation may not be required in some systems. For example, the sensors can be located in serial alignment on the catheter 10. A further alternative includes proximally locating the sensors.

According to one aspect of the invention, the temperature adapter 24 and Foley catheter 10 are used in conjunction with vascular heat exchange catheter. It can be appreciated that core body temperature measurements are important to facilitate proper functioning of any system that regulates the core body temperature of a patient. Accordingly, redundant bladder temperature measurements with collocated sensor elements 33 and 35, is desirable to minimize any risk or inconvenience associated with temperature monitoring failure.

In one embodiment, the temperature sensor elements 33 and 35 electronically couple with a control unit, which obtains a primary temperature reading from one of the temperature sensor elements and obtains a secondary temperature reading from the other temperature sensor elements. The control unit compares the primary and secondary temperature reading to determine a difference.

Foley catheters can be used to drain urine for several weeks. An integrated temperature sensor 46, may fail during this period. In one embodiment, a method in accordance with the present invention enables an introduced Foley catheter having a failed integrated temperature sensor to be used continuously for draining urine notwithstanding failure of the integrated temperature sensor 46. The steps of maintaining the catheter 10 in the bladder 42 and attaching the adapter 24 to the proximal end 14 and advancing the adapter temperature sensor 38 provides a secondary measure of temperature without requiring the unpleasant steps of removal and replacement of the Foley catheter 10.

Figure 3:
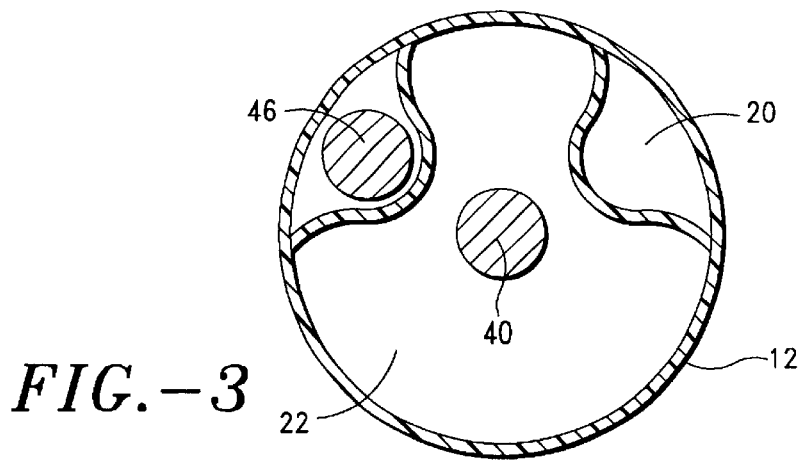
FIG. 3 is a cross-sectional view of the catheter body as seen along the line 3—3 in FIG. 4 is an exploded cross-sectional view of the cap and fitting in accordance with the present invention.

FIG. 3 shows the catheter body 12 having three lumens, the inflation lumen 20, the drainage lumen 22, and an integrated temperature sensor lumen 48. The temperature sensor lumen 48 houses the wire 46 of the integrated temperature sensor 46. The wire 40 of the adapter temperature sensor 38 is positioned freely in the drainage lumen 22.

Figure 4:
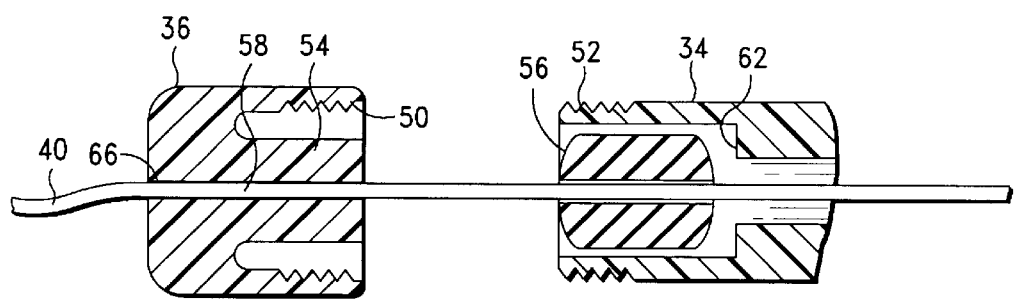

FIG. 4 shows the cap 36, the fitting 34 and a seal 56. The cap 36 has internal threads 50 and the fitting 34 has external threads 52. The cap 36 has an axis and includes an axially disposed post 54. The seal 56 seats within the fitting 34. The post 54 defines a portion of a channel 58. The channel 58 extends axially through the cap 36, the fitting 34 and the seal 56. The temperature sensor wire 40 normally slides through the channel 58 when the cap 36 and the fitting 34 loosely engage, or disengage.

According to an aspect of the invention, the seal 56 is generally cylindrical in shape and circumscribes the wire 40. The wire 40 is lubricated to facilitate sliding when the cap 36 loosely fits on the fitting 34.

The fitting 34 defines an annular flange 62 so that when the cap 36 threads on to the fitting 34, the post 54 of the cap 36 presses the seal 56 against the annular flange 62. Rotation of the cap 36 with respect to the fitting 34 deforms the seal 56, which grips the wire 40 and thereby selectively anchors the wire 40 with respect to the cap 36 and the fitting 34.

Figure 5:
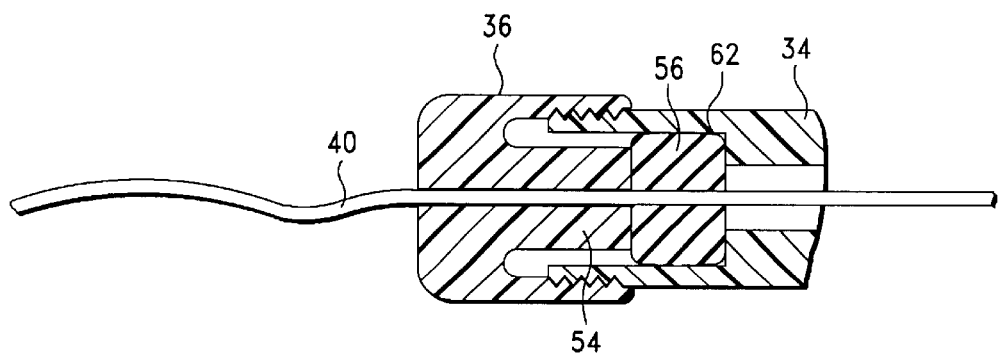
FIG. 5 is a cross-sectional view of the cap operatively engaged with the fitting as seen along the line 5—5 of FIG. 2.

FIG. 5 shows the cap 36 engaging the fitting 34. The cap 36 rotates to compress the seal 56 against the flange 62. The seal 56 circumscribes the wire 40 so that compressing the seal 56 anchors the wire 40.

Figure 6:
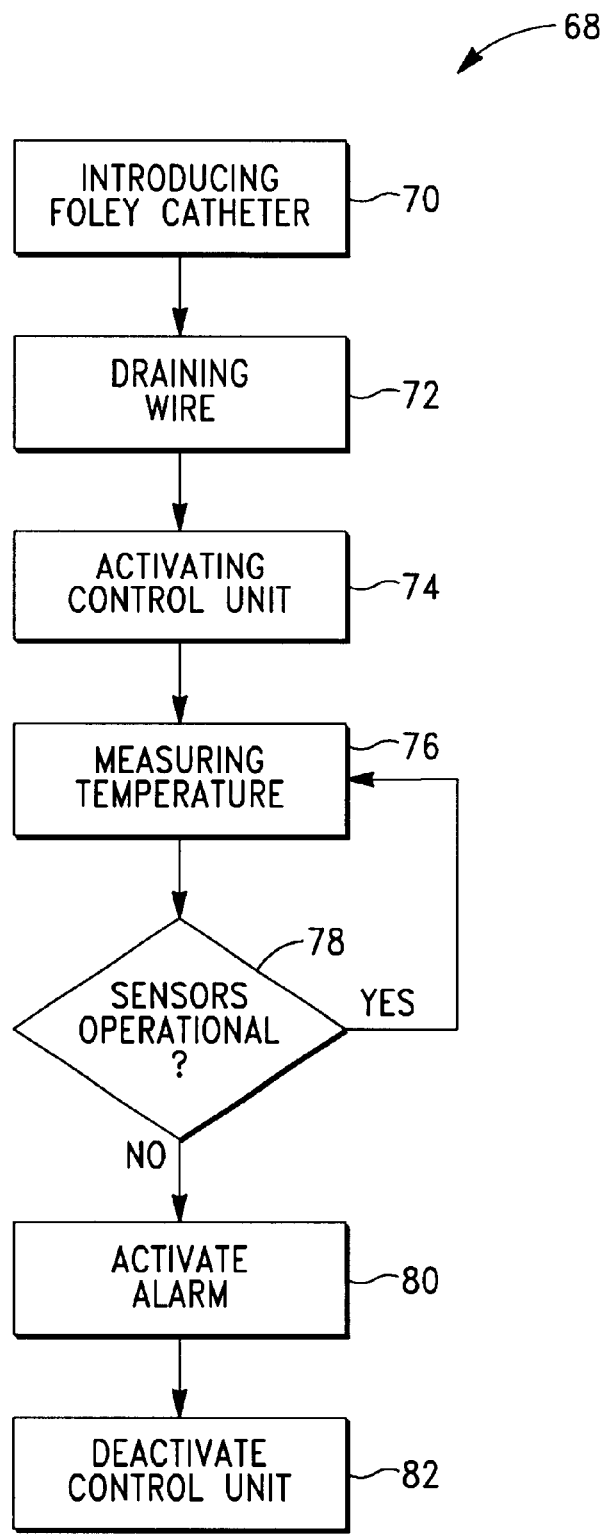
FIG. 6 is a method in accordance with the present invention.

FIG. 6 shows a method generally designated with the reference numeral 68. The method includes the steps of introducing a Foley catheter 70 having redundant temperature sensors into the bladder of a patient for the purpose of measuring patient core body temperature. The next step includes using the Foley catheter to drain urine 72 from the bladder.

Once the Foley catheter is in place in the patient and operates, the step of activating a control unit 74 follows. The sensors measure temperature 76 within the bladder of the patient and the control unit reads the temperature measurements.

The next step performed by the control unit is to monitor the temperature sensors for operability and accuracy and decide if sensors are operational 78. If the sensors are both operational and provide consistent temperature readings, the control unit continues operation. However when the sensors measure a temperature difference greater than an established threshold between the sensors, the control unit assumes that one sensor has failed and activates an alarm 80. Once the alarm is activated, the control unit performs the step of deactivating the control unit 82.

It can be appreciated that the control unit will also activate an alarm 80 and deactivate the control unit 82 when one of the sensors fails to provide a signal.

According to one aspect of the invention the draining step 72 and the activating step occur in parallel. According to a further aspect of the invention, the alarm step 80 and the deactivation step 80 occur in parallel.

Figure 7:
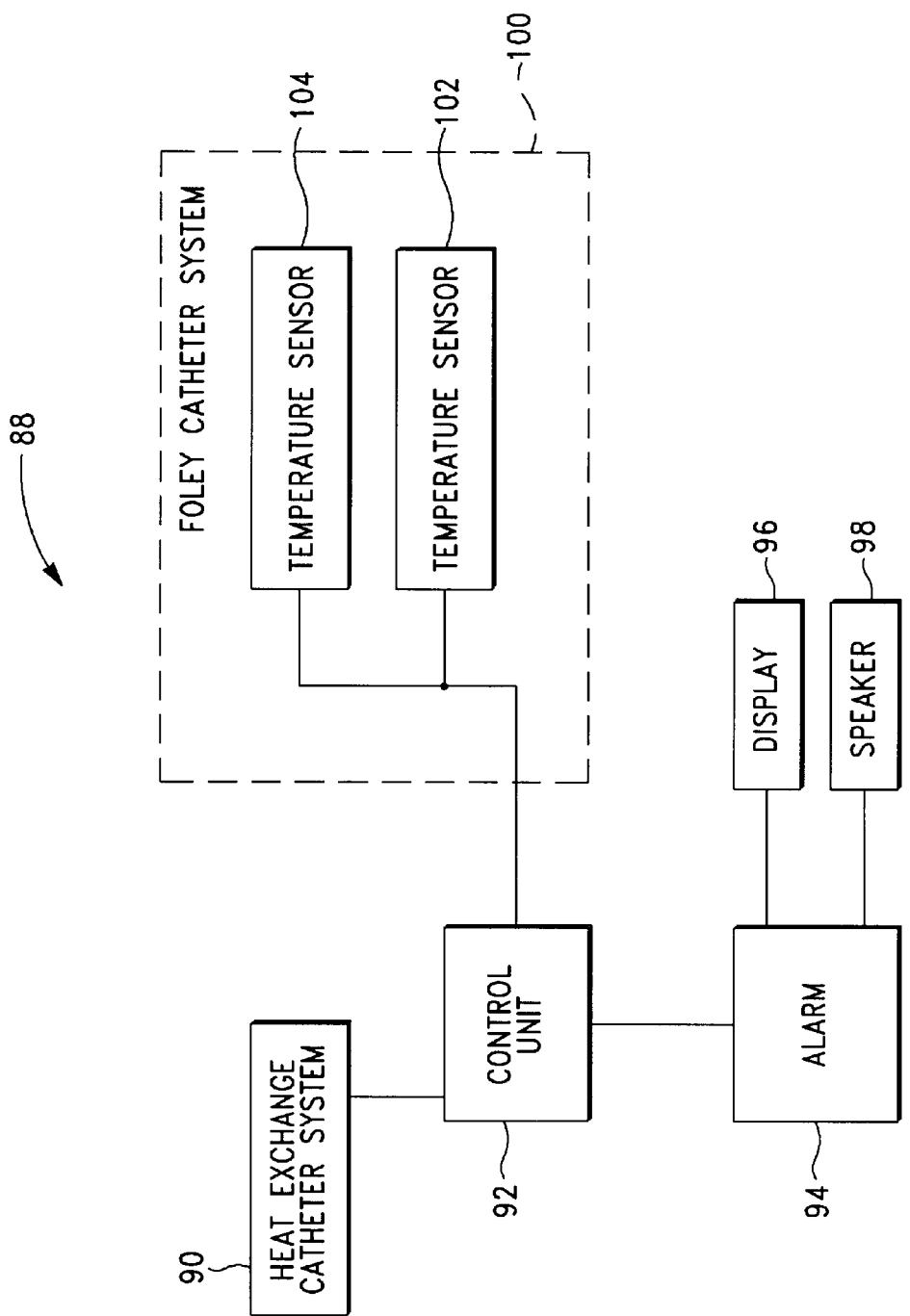
FIG. 7 is a system in accordance with the present invention.

FIG. 7 shows a system generally designated with the reference numeral 88. The system includes a heat exchange catheter system 90, a control unit 92 with an alarm 94, a display 96 and a speaker 98. The system 88 also includes a Foley catheter system 100 having redundant temperature sensors -102 and 104. The control unit 92 operates the heat exchange catheter system 90 and monitors Foley catheter system 100.

The control unit 92 regulates operation of the heat exchange catheter system 90 to maintain patient temperature, to heat the patient, or to cool the patient. The control unit 92 relies on patient core body temperature, or local body temperature, measurements from temperature sensors 102 and 104. According to one aspect of the invention, the core body temperature measurement is provided to the control unit 92 by the Foley catheter system 100. The Foley catheter system 100 includes a Foley catheter having two integrated temperature sensors 104 and 102.

The sensors 102 and 104 electronically communicate with the control unit 92 to provide redundant temperature measurement signals to the control unit 92. The control unit establishes a threshold. When signals from the sensor 102 and 104 are indicative temperatures beyond the established threshold, then the control unit 92 assumes that one of the sensors is non-operational and shuts down the heat exchange catheter system 90. Likewise when one of the temperature sensors 102 or 104 completely fails, yielding no temperature signal, then the control unit 92 shuts down the heat exchange catheter system 90.

The control unit 92 includes the alarm 94, which includes the display 96 and the speaker 98. Activating the alarm 94 either displays a notice on the display 96, or projects sound through the speaker 98, or both, to notify an operator when a sensor 102 or 104 has failed. By default, the control unit 92 shuts down the heat exchange catheter system 90 and deactivates itself when either of the sensors 102 or 104 fail.

IN USE

An anticipated use for the invention described herein is in conjunction with a patient temperature regulation system having a heat exchange catheter. A system having a heat exchange catheter is described generally in U.S. Pat. Nos. 6,146,411 and 6,019,783, the disclosures of which are incorporated by reference. A feedback loop between the temperature sensor of the Foley catheter and the patient temperature regulation system is established.

A typical patient temperature regulation system includes a venous catheter having a heating and/or cooling element. The catheter inserts into a patient's central venous system to warm and/or cool the blood. The warmed/cooled blood circulates within the patient to effect the patient core body temperature. In accordance with the present invention, the core body temperature is measured using a Foley catheter and adaptor as described herein.

A heat exchange catheter and system are described in U.S. Pat. Nos. 6,146,411 and 6,126,684, the disclosures of which are incorporated herein by reference. One heat exchange catheter includes lumens for circulating heat exchange fluid within the catheter. This creates a closed system heat exchanger so that circulation of heat exchange fluid within the catheter cools/warms the blood of the patient. A system employing the heat exchange catheter has a temperature measurement device and a control unit. The control unit regulates the rate of flow of the heat exchange fluid as well as the temperature of the fluid. The control unit also monitors the temperature sensors in an embodiment of the invention having redundant temperature sensors.

A feedback loop established between the Foley catheter-based temperature sensor elements of the present invention is used to regulate the heat exchange fluid temperature of the closed system, and the rate of heat exchange fluid flow.

While the present invention is anticipated to be used in conjunction with a patient temperature regulation system, it can be appreciated that it can be used in any of a number of systems. For example, the present invention can be used in virtually any surgical procedure requiring a measurement of a patient's core body temperature.

What is claimed is:

1. A method for measuring and regulating patient temperature comprising:

introducing a heat exchange catheter into the vasculature of a patient to regulate patient temperature;

introducing a Foley catheter having a drainage lumen and redundant temperature sensors into the bladder of the patient;

draining urine from the bladder via the drainage lumen;

electronically connecting a control unit with the temperature sensors;

measuring patient core body temperature with the temperature sensors; and determining if one of the temperature sensors has failed.

2. A method as set forth in claim 1 further comprising obtaining a primary temperature reading and a secondary temperature reading from the temperature sensors.

3. A method as set forth in claim 2, further comprising:

comparing the primary temperature reading and the secondary temperature reading to determine a difference between the primary temperature reading and the secondary temperature reading.

4. A method as set forth in claim 3, further comprising:

establishing a threshold; and activating an alarm when the difference between the primary temperature and the secondary temperature exceeds the threshold.

5. A method as set forth in claim 3, further comprising:

establishing a threshold; and deactivating the control unit when the difference between the primary temperature and the secondary temperature exceeds the threshold.

6. A method as set forth in claim 5, wherein the threshold is within the range of 0.5–2 degrees Fahrenheit.

7. A method as set forth in claim 5, wherein the threshold is about 1 degree Fahrenheit.

* * * * *